United States Patent [19]
Stahl

[11] 3,964,165
[45] June 22, 1976

[54] ELASTOMERIC ORTHODONTIC APPARATUS

[76] Inventor: Lee W. Stahl, 4325 Mockingbird Lane, Toledo, Ohio 43623

[22] Filed: May 23, 1974

[21] Appl. No.: 472,618

[52] U.S. Cl. ............................................. 32/14 A
[51] Int. Cl.² ....................................... A61C 7/00
[58] Field of Search .............................. 32/14 A

[56] References Cited
UNITED STATES PATENTS

| | | | |
|---|---|---|---|
| 3,423,833 | 1/1969 | Pearlman | 32/14 A |
| 3,464,112 | 9/1969 | Silverman et al. | 32/14 A |
| 3,496,637 | 2/1970 | Etengoff | 32/14 A |
| 3,626,593 | 12/1971 | Ridgeway | 32/14 A |
| 3,765,091 | 10/1973 | Northcutt | 32/14 A |

*Primary Examiner*—Robert Peshock
*Attorney, Agent, or Firm*—David H. Wilson

[57] ABSTRACT

An orthodontic apparatus for use with a single straight arch wire in both the edgewise and the light-wire techniques to apply a continuous gentle pressure to teeth. One embodiment of the apparatus has a wire retaining bracket made of an elastomeric vinyl polymer which is banded to or molded integral with a band which is affixed to a tooth. The bracket has a pair of parallel upstanding wings which include a horizontal slot and retaining tips for retaining the arch wire. The horizontal slot has a liner formed of a substantially rigid material with the retaining tips formed on the upper and lower walls thereof. The wings have generally triangularly shaped tying tips for use with a ligature wire or elastic connector to apply pressure to a tooth. The tying wing tips also may have horizontal apertures therein for receiving a ligature wire. The bracket also has a vertical tubular aperture extending therethrough for retaining an attachment pin of a "C-clamp" appliance. The wings may also have auxillary springs affixed thereto to generate forces on adjacent teeth. The elastomeric material is easily deflected yet generates a force as it attempts to return to its free shape which aids in straightening the teeth. In another embodiment, the apparatus is a tube made from an elastomeric vinyl polymer which is slipped over the arch wire to apply pressure between two points.

8 Claims, 24 Drawing Figures

ELASTOMERIC ORTHODONTIC APPARATUS

BACKGROUND OF THE INVENTION

1. Field of the Invention

The invention relates in general to orthodontic apparatus for performing orthodontic treatment and in particular to elastomeric orthodontic bands and brackets for use with arch wires and elastic connectors.

2. Description of the Prior Art

In the science of orthodontics there has been developed two techniques and the associated apparatus for straightening teeth. The "edgewise" technique was developed first and employs orthodontic brackets having a horizontal slot for receiving a single rectangular arch wire. The arch wire is retained by brackets attached to adjacent teeth and is bent to achieve "tipping" (rotation of the tooth about the buccal-lingal axis toward or from adjacent teeth) or "torquing" (rotation of the tooth about the mesial-distal axis toward or from the palate). The rectangular arch wire is usually relatively large in diameter and is painful to the patient since large rotational forces are generated.

The "light-wire" technique was developed in an attempt to avoid the painfully large rotational forces of the "edgewise" technique. A thin round wire is utilized to reduce the rotational foces while achieving results which are as effective as those obtained with large rectangular or round wires. In addition there is less friction between the bracket and the wire so that the teeth can move much more easily.

Early prior art orthodontic devices were made from metal which was strong but not aesthetically pleasing. U.S. Pat. No. 3,504,438 issued to H. P. Wittman et al shows an orthodontic appliance comprising a band and a bracket with an exterior surface covering of a polymeric material such as Teflon which not only produces a pleasing aesthetic appearance but also has a low coefficient of friction to aid in the movement of the teeth. A further development is shown in the Northcutt U.S. Pat. No. 3,765,091 wherein an orthodontic onlay is an integral rigid plastic member which will not give to the forces applied by the arch wire. The plastic material may be clear or may be tooth color to provide a pleasing aesthetic appearance.

SUMMARY OF THE INVENTION

The present invention comprises an orthodontic apparatus for use with a single straight arch wire in both the edgewise and the light-wire techniques for straightening teeth. In one embodiment the apparatus has a tooth colored or clear elastomeric vinyl polymer bracket for retaining the arch wire which is bonded to or molded integral with a band which is affixed to the tooth. The bracket has a pair of parallel upstanding wings which include a horizontal slot and retaining tips for retaining an arch wire. The horizontal slot has a substantially rigid liner that will deflect to allow the arch wire to snap past the retaining tips and then will return to its original shape to retain the wire in the slot. The wings have generally triangularly shaped tying tips for use with a ligature wire or an elastic connector where the arch wire cannot be reached with the slots in the bracket. The tying tips also may have a horizontal aperture therein for receiving a ligature wire. Since the wings are made of an elastomeric material, they will deflect and apply force to a tooth through a ligature wire or an elastic connector. The bracket also has a vertical tubular aperture extending between the wings for retaining an attachment pin or a "C-clamp" appliance. The wings may also have auxillary springs affixed thereto to generate forces to separate or draw together adjacent teeth.

In another embodiment of the present invention, the apparatus takes the form of a tube made from an elastomeric vinyl polymer which is slipped over the arch wire to apply pressure between two points along the arch wire.

It is an object of the present invention to provide an orthodontic apparatus which produces a pleasing aesthetic appearance.

It is another object of the present invention to provide an orthodontic apparatus for utilizing the "light-wire" technique wherein ligature wires or elastic connectors may be utilized as required.

A further object of the present invention is to provide an orthodontic apparatus which reduces the installation and removal time of an orthodontic system.

Still another object of the present invention is to provide an orthodontic apparatus formed of an elastomeric material which evenly applies force to a tooth to be straightened.

Another object of the present invention is to provide an orthodontic apparatus in which auxillary springs may be utilized in straightening teeth to provide more control.

Another object of the present invention is to provide an orthodontic apparatus in which attachment pins may be utilized to facilitate the application of the force applied to a tooth to be straightened.

BRIEF DESCRIPTION OF THE DRAWINGS

The above, as well as other, objects and advantages of the invention will become readily apparent to one skilled in the art from reading the following detailed description of an embodiment of the invention when considered in the light of the accompanying drawings, in which:

FIG. 16a is a front elevational view of the attachment pin of FIG. 15.

FIG. 16b is a side elevational view of the attachment pin of FIG. 16a.

FIG. 16c is an enlarged cross-sectional view taken along line 16c—16c of FIG. 16a.

DESCRIPTION OF THE PREFERRED EMBODIMENT

Figure 1:
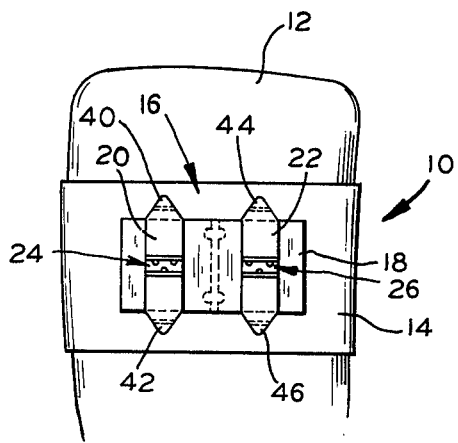
FIG. 1 is a front elevational view of the preferred embodiment of the present invention shown affixed to a tooth.
Figure 2:
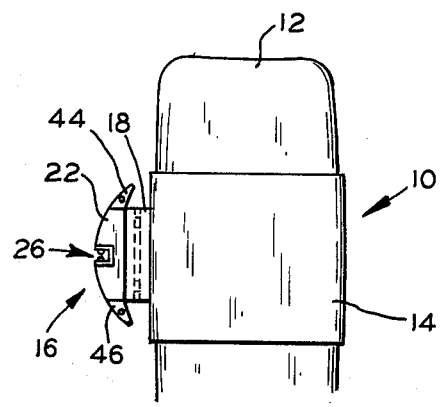
FIG. 2 is a side elevational view of the present invention as shown in FIG. 1.

Referring to FIGS. 1 and 2, there is shown an orthodontic apparatus 10, according to the present invention, mounted on a tooth 12. The apparatus 10 comprises a band 14 affixed to the tooth 12 in a conventional manner, such as by dental cement, and a bracket 16 attached to the band 14. The band 14 may be formed of metal, typically a stainless steel alloy or aluminum, which is ductile while being formed around the tooth. The outwardly facing buccal or labial surface of the band 14 is coated with a plastic tooth colored material to produce a pleasing aesthetic appearance. The band 14 may also be formed in two sections joined together with a metal ligual or inwardly facing section and a clear or tooth colored elastomeric vinyl polymer buccal section. Furthermore, the band 14 may be formed of two sections wherein the end portions of the sections are in an overlapping or abutting relationship to allow relative movement between them. The sections would be encased in a tooth colored elastomeric material which would not inhibit such relative movement but would tend to draw the band sections to the tooth. Such a construction would provide for a better fit between the tooth and the band.

Figure 4:
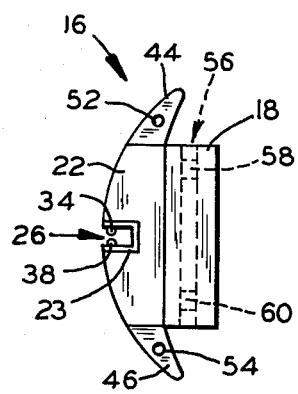
FIG. 4 is a side elevational view of the bracket shown in FIG. 3.
Figure 5:
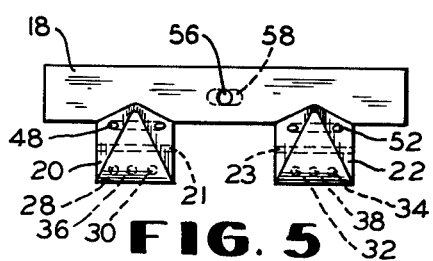
FIG. 5 is a top elevational view of the bracket shown in FIG. 3.
Figure 6:
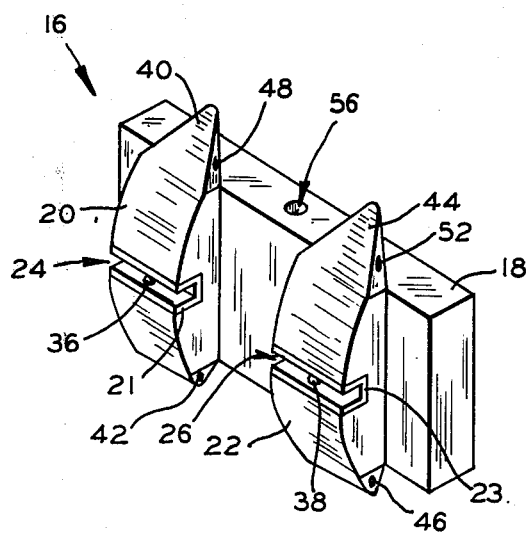
FIG. 6 is an enlarged perspective view of the bracket shown in FIG. 3.

The bracket 16 is formed of a clear or tooth colored elastomeric vinyl polymer and is bonded to the metal buccal surface or is made integral with the vinyl polymer buccal section. The band and bracket may also be molded as an integral device of an elastomeric material. Referring to the enlarged elevational views FIGS. 3 to 5 and the enlarged perspective view FIG. 6, there is shown the bracket 16 having a base portion 18 and a parallel pair of upstanding wings 20 and 22. Each of the wings 20 and 22 has a liner, 21 and 23 respectively which define a horizontal slot, 24 and 26 respectively, of rectangular cross-section formed in the buccal surface thereof for receiving an arch wire. Projecting from the upper wall of each of the slots 24 and 26 is a pair of retaining tips, 28 and 30 in the slot 24 and 32 and 34 in the slot 26, which cooperate with a pair of retaining tips 36 and 38 projecting from the lower walls of the slots 24 and 26 respectively and centered between the upper retaining tips. The width of the slots 24 and 26 is slightly greater than the diameter of an arch wire, whereas the distance between the upper and lower retaining tips is slightly less than the diameter of the arch wire to retain the wire in the slots thereby eliminating the previous requirement for ligature wires or elastic connectors. The arch wire can be threaded through the slots from the open ends or may be snapped past the retaining tips. The liners 21 and 23 are made of metal or a substantially rigid plastic such as Lexan which is strong enough to retain the arch wire against the pressures applied to the teeth. The bracket may be molded around the liner to form an integral unit.

Each of the wings 20 and 22 has a pair of generally triangular shaped tying wing tips, 40 and 42 for the wing 20 and 44 and 46 for the wing 22, which may be utilized where a seriously malposed tooth is too far from the arch wire to allow the wire to be snapped into the slots 24 and 26. The front surfaces of the wings 20 and 22 are curved about the horizontal axis to form an arc which is subtended by the tying wing tips. A ligature wire or an elastic connector may be affixed between one or more tying wing tips on the bracket affixed to the malposed tooth and the arch wire and/or a bracket affixed to an adjacent tooth. The terminal ends of the tying wing tips 40, 42, 44 and 46 are gently rounded to facilitate the installation and removal of the elastic connectors. Each of the tying wing tips 40, 42, 44 and 46 also may have a horizontal tubular aperture formed therein 48, 50, 52 and 54 respectively which can be utilized for receiving a ligature wire when required.

Figure 16:
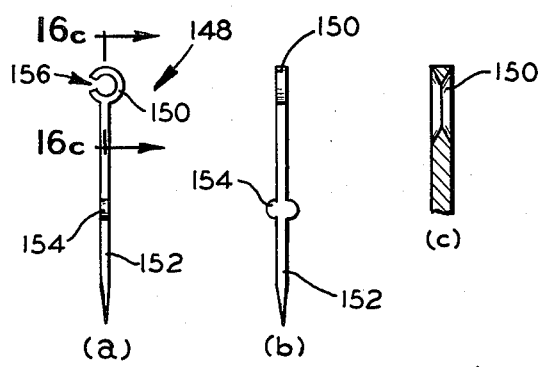

The bracket 16 also has a vertical tubular aperture 56 formed in the base portion 18 thereof which is substantially parallel to the wings 20 and 22. The aperture 56 has formed therein a pair of pin retaining cavities 58 and 60 which receive the enlarged portion of an attachment pin as shown in FIGS. 16a and 16b. The attachment pin can be inserted into the vertical aperture 56 at either end and the elastomeric material will give to increase the diameter of the vertical aperture as the pin is moved to one of the cavities 58 or 60 where it will be retained.

Figure 7:
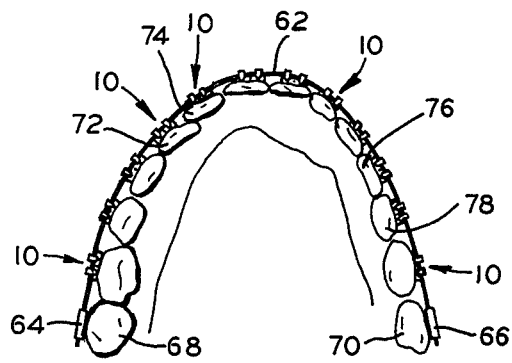
FIG. 7 is a plan view of a typical set of teeth showing one of the present invention affixed to each tooth and interconnected by an arch wire.
Figure 8:
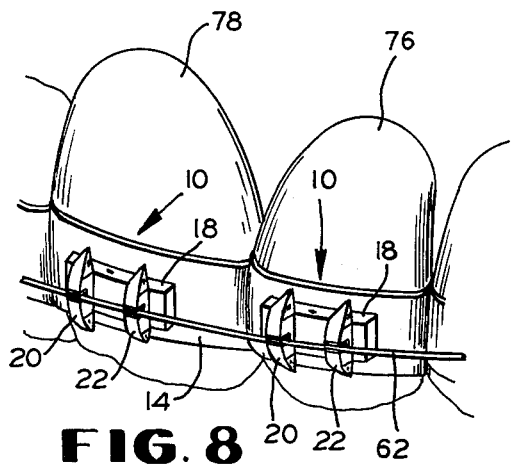
FIG. 8 is an enlarged fragmentary perspective view of two adjacent teeth having the present invention affixed thereto as shown in FIG. 7.
Figure 9:
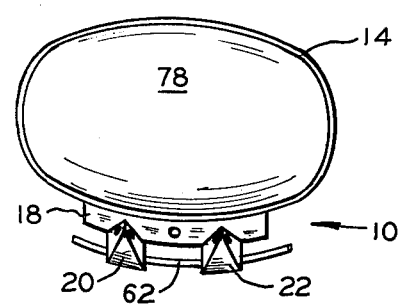
FIG. 9 is a plan view of the present invention as shown in FIG. 8.
Figure 10:
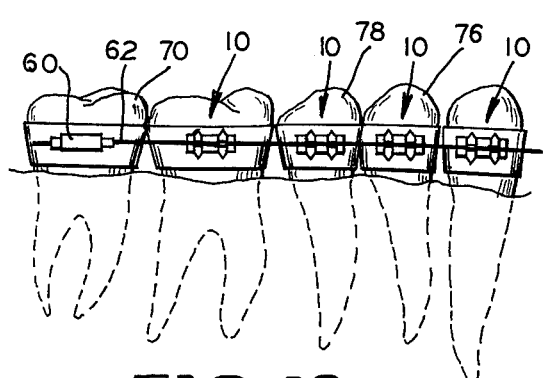
FIG. 10 is a fragmentary elevational view of the present invention affixed to several teeth as shown in FIG. 7.

Referring to FIGS. 7, 8, 9 and 10, there is shown the present invention utilized with a straight arch wire. FIG. 7 is a plan view of a typical set of teeth showing one of the orthodontic apparatus 10 according to the present invention attached to each tooth and interconnected by an arch wire 62. The ends of the arch wire are anchored by a pair of buccal tubes, 64 and 66, affixed to the molars 68 and 70. The buccal tubes may have circular or rectangular longitudinal apertures formed therein for receiving a round or rectangular arch wire. The arch wire 62 has been formed into the shape of the outline of the desired positions for the teeth and then is snapped into the brackets affixed to the teeth. Where there is a malposed tooth, such as a tooth 72 which has grown partially behind a tooth 74, the arch wire is deflected and tends to exert a force on the tooth 72 to move it to the desired position. However, the force generated is not great enough to snap the arch wire 62 past the retaining tips of the bracket. The elastomeric bracket is also distorted and applies an additional force to move the tooth 72 to the desired position. FIG. 8 is an enlarged perspective view of a pair of adjacent teeth 76 and 78 of FIG. 7. Each of the teeth 76 and 78 has an orthodontic apparatus 10 affixed thereto and is connected by the arch wire 62. FIG. 9 is a plan view of the tooth 78 in FIGS. 7 and 8 showing the orthodontic apparatus 10 formed to the curvature of the tooth 78. FIG. 10 is a fragmentary elevational view of the set of teeth of FIG. 7 showing the buccal tube 66 attached to the molar 70 to anchor the arch wire 62.

Figure 11:
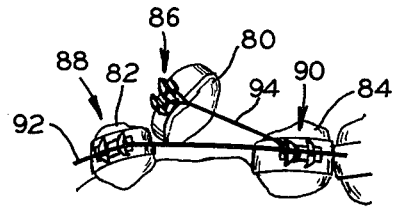
FIG. 11 is a fragmentary perspective view of the present invention as utilized with an elastic connector to rotate a tooth to a straight arch wire.
Figure 12:
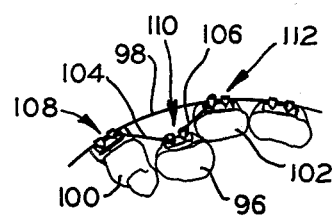
FIG. 12 is a fragmentary perspective view of the present invention as utilized with a pair of elastic connectors to bring a tooth to a straight arch wire.
Figure 13:
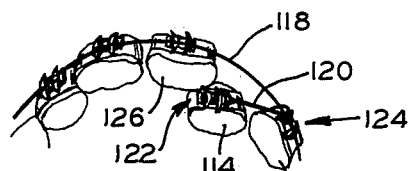
FIG. 13 is a fragmentary perspective view of the present invention as utilized with an elastic connector to bring a tooth to a straight arch wire.

Referring to fragmentary perspective views FIGS. 11, 12 and 13, there is shown the present invention as utilized with elastic connectors to bring teeth to a straight arch wire. In FIG. 11, a malposed tooth 80 and a pair of adjacent teeth 82 and 84 each have an orthodontic apparatus, 86, 88 and 90 respectively, affixed thereto. A straight arch wire 92 is snapped into the brackets of the devices 88 and 90 but cannot reach the device 86 without a sharp bend which would destroy the ability of the arch wire to force the tooth 80 into the desired position between the teeth 82 and 84. Therefore, an elastic connector 94 is stretched between a wing of the device 86 and a wing of the device 90. The elastic connector 94 exerts a force which tends to rotate the tooth 80 to the desired position. As the tooth 80 moves, shorter elastic connectors may be utilized to maintain a straightening force until the tooth 80 is close enough to the arch wire 92 for the arch wire to be snapped into the bracket of the device 86. The elastic connector 94 may typically be an AlastiK Force Module manufactured and sold by the Unitek Corporation of Monrovia, California. These connectors are transparant and will blend with the orthodontic apparatus of the present invention to provide a pleasing aesthetic appearance.

In FIG. 12, there is shown a tooth 96 which must be brought to an arch wire 98. Since the tooth 96 is relatively straight in relation to a pair of adjacent teeth 100 and 102, a pair of elastic connectors 104 and 106 are utilized to draw the tooth 96 to the arch wire 98 without rotation as was required with the tooth 80 of FIG. 11. The connector 104 is stretched between a wing of an orthodontic apparatus 108 affixed to the tooth 100 and a wing of an orthodontic apparatus 110 affixed to the tooth 96. The second connector 106 is stretched between a wing of an orthodontic apparatus 112 and the other wing of the orthodontic apparatus 110.

In FIG. 13, there is shown a tooth 114, which must be drawn toward an adjacent tooth 116 before it is drawn to an arch wire 118. An elastic connector 120 is stretched between a wing of an orthodontic apparatus 122 affixed to the tooth 114 and a wing of an orthodontic apparatus 124 affixed to the tooth 116. After the tooth 114 has been moved into the gap between the tooth 116 and another tooth 126 a second elastic connector can be stretched between the other wing of the orthodontic apparatus 122 and a wing of an orthodontic apparatus 128 affixed to the tooth 126.

Figure 14:
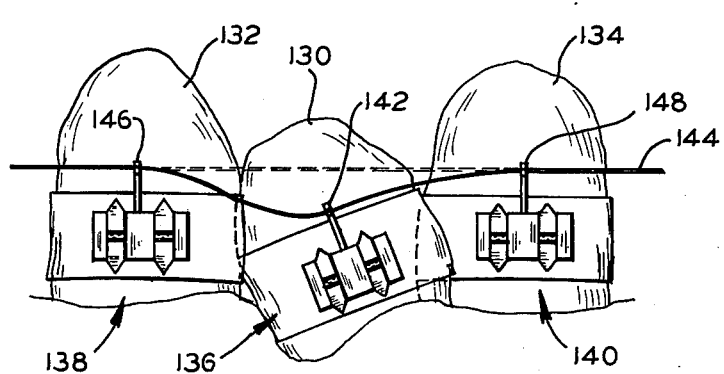
FIG. 14 is a fragmentary perspective view of the present invention affixed to three teeth wherein the middle tooth must be rotated utilizing attachment pins.

Referring to FIG. 14, there is shown a fragmentary perspective view of a malposed tooth 130 positioned partially behind an adjacent tooth 132 and partially in front of an adjacent tooth 134. The teeth 130, 132 and 134 each have an orthodontic apparatus, 136, 138 and 140 respectively affixed thereto. An attachment pin 142 is retained by the vertical aperture in the orthodontic apparatus 136 and is attached to a light wire 144. The light wire 144 is also attached to an attachment pin 146 which is retained by the vertical aperture in the orthodontic apparatus 136 and an attachment pin 148 which is retained by the vertical tubular aperture in the orthodontic apparatus 134. The pins 146 and 148 are utilized where the malposed tooth 130 must be leveled before the orthodontic apparatus 136 can be attached to an arch wire thereby drawing the tooth into the space between the teeth 132 and 134 as shown by the position of the dashed light wire 144.

Figure 15:
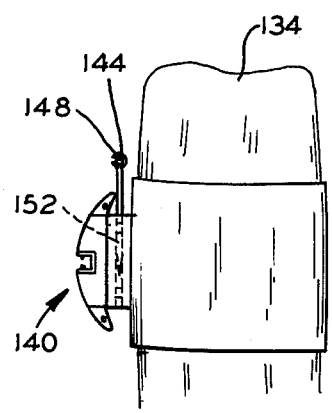
FIG. 15 is a side elevational view of the present invention affixed to a tooth showing a retained attachment pin of FIG. 14.

FIG. 15 is a side elevational view of the tooth 134 of FIG. 14 showing the attachment pin 148 secured in the vertical tubular aperture of the orthodontic apparatus 140. The arch wire is snapped through a small opening in the hook portion of the pin 148. Referring to FIGS. 16a and 16b, there is shown the attachment pin 148 of FIG. 15 in a front and a side elevational view, respectively. The pin 148 is comprised of a hook portion 150 and a body portion 152. The body portion 152 includes a pair of semi-circular tabs 154 extending from the sides thereof which cooperate with the pin retaining cavities 58 and 60 of FIG. 3 to positively hold the pin in the vertical tubular aperture. The body portion 152 also has a pointed end opposite the hook end which facilitates the insertion of the pin into the vertical tubular aperture. The hook portion 150 has a V-shaped cross-section as shown in the enlarged cross-sectional view of FIG. 16c taken along line 16c—16c of FIG. 16a. The hook portion 150 also has an opening 156 through which an arch wire may be snapped. The upper section of the body portion 152 may also be offset from the lower section to move the point of application of a force nearer the center of the overall length of the tooth.

Figure 17:
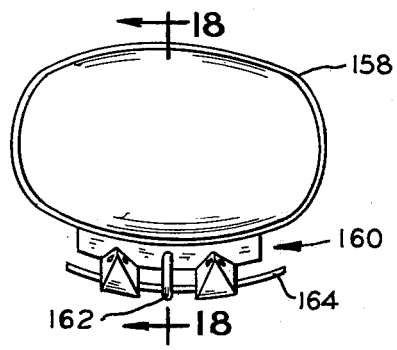
FIG. 17 is a plan view of the present invention utilizing a "C-clamp" for retaining the arch wire.
Figure 18:
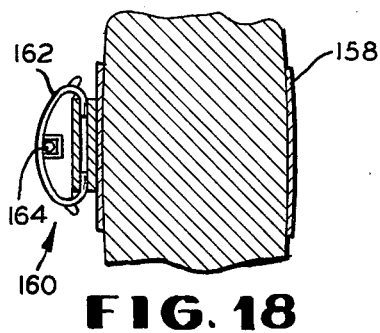
FIG. 18 is a cross-sectional view taken along line 18—18 of FIG. 17.

FIG. 17 is a plan view of an orthodontic apparatus 158 affixed to a tooth 160. A "C-clamp" appliance 162 can be snapped into both ends of the vertical tubular aperture to aid in retaining an arch wire 164 in the arch wire slots when the arch wire is under a relatively large pressure forcing it from the slots. The "C-clamp" appliance may be formed from a metal wire having an elastomeric coating. FIG. 18 is a cross-sectional view taken along the line 18—18 of FIG. 17.

Figure 19:
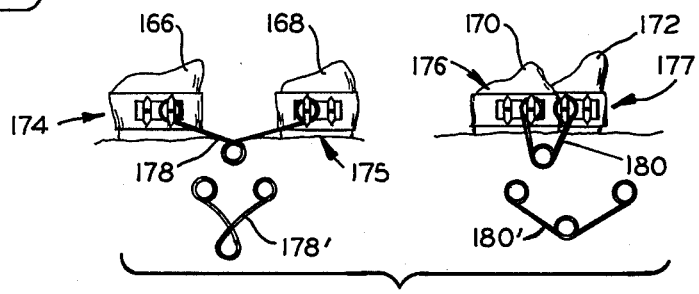
FIG. 19 is a fragmentary elevational view of the present invention affixed to several teeth including auxillary springs.

FIG. 19 is a fragmentary elevational view of four teeth 166, 168, 170 and 172 having an orthodontic apparatus 174, 175, 176 and 177 respectively, affixed to each one. A pair of auxillary springs 178 and 180 are shown to illustrate another function of the wings of the orthodontic apparatus. The spring 178 represents a spring of less than one coil whereas the spring 180 respresents a spring of more than one coil. A loop is formed at both ends of the springs so that they may be attached to the wings of the orthodontic apparatus. The loops can be expanded to fit over the tying wing tips and then will contract to their free diameters so that they are retained by the wing tips. If the distance between the wings to which the spring 180 is attached is less than the distance between the free spring ends, as shown by the spring 180', the spring will tend to force the adjacent teeth apart. If the distance between the wings to which the spring 178 is attached is greater than the distance between the free spring ends, as shown by the spring 180', the spring will tend to pull the adjacent teeth together. Therefore, the desired function can be obtained by selecting the proper type of spring with the correct end to end distance.

Figures 20, 21:
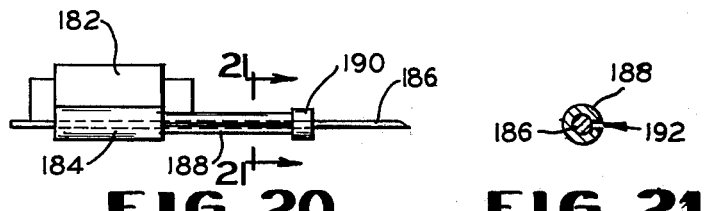
FIG. 20 is a fragmentary elevational view of another embodiment of the present invention as utilized with a buccal tube.
FIG. 21 is an enlarged cross-sectional view taken along line 21—21 of FIG. 20.

Referring to FIG. 20, there is shown a combination buccal tube having an upper buccal tube 182 for retaining the ends of a face bow and a lower buccal tube 184 for slidably retaining the ends of an arch wire 186. An elastomeric coil 188, made from an elastomeric material that is clear or tooth colored and formed in the shape of a tube, can be slipped over the arch wire 186 and compressed between the lower buccal tube 184 and a stop piece 190 attached to the arch wire 186 to apply pressure to the arch wire for expansion of the teeth. As shown in FIG. 21, an enlarged cross-sectional view taken along the line 21—21 of FIG. 20, the elastomeric coil is generally "C" shaped and may have a longitudinal opening 192 which allows the coil 186 to be snapped over the arch wire 186 as the elastomeric material gives.

Figure 22:
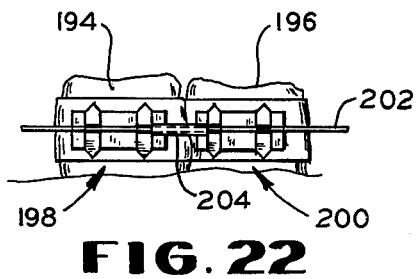
FIG. 22 is a fragmentary elevational view of an elastomeric coil as utilized to move adjacent teeth away from one another.

The elastomeric coil may also be utilized to apply pressure to the brackets of the present invention. Referring to FIG. 22, there is shown a pair of teeth 194 and 196 which are too closely spaced. Each tooth has an orthodontic apparatus 198 and 200 affixed thereto with an arch wire 202 retained by the brackets. An elastomeric coil 204 having a length longer than the spacing between the adjacent wings of the brackets is slipped on the arch wire 202 which is then inserted into the slots in the wings to compress the coil. The compressed elastomeric coil exerts a gentle continuous pressure over a long period of time to move the teeth 194 and 196 apart. Thus, the elastomeric coil 204 may be utilized in place of the auxillary spring 180 of FIG. 19. These coils may be supplied in a relatively long continuous section from which individual coils could be cut in the desired lengths.

Figure 3:
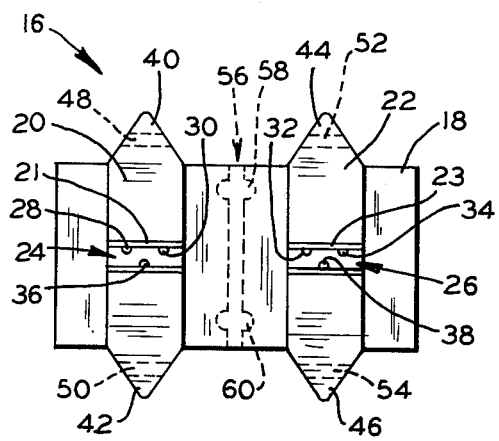
FIG. 3 is an enlarged front elevational view of the bracket shown in FIG. 1.
Figure 23:
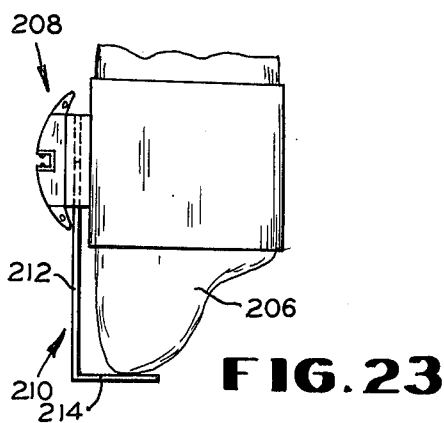
FIG. 23 is a side elevational view of a positioning guide as utilized with a bracket of the present invention.

The vertical tubular aperture 56 formed in the base portion 18 of the bracket 16 as shown in FIG. 3 may also be utilized to retain a positioning guide. Referring to FIG. 23, there is shown a tooth 206 to which an orthodontic apparatus 208 has been affixed. A positioning guide 210, having a pair of semi-circular tabs extending from the body portion 212 thereof which are similar to the tabs 154 of the attachment pin 148 of FIG. 166, is retained in the vertical tubular aperture of the bracket of the orthodontic apparatus 208. A guide portion 214 is formed at approximately a right angle to the body portion 212 and at the correct distance for positioning the apparatus 208 on the tooth 206. The positioning guide 210 is inserted into the vertical tubular aperture of the orthodontic apparatus 208 until the tabs snap into the retaining cavities. Then the orthodontic apparatus is slipped over the end of the tooth 206 until the guide portion 214 contracts the tooth to indicate the correct positioning. After the cement has set to affix the orthodontic apparatus to the tooth, the positioning guide 210 may be removed.

Figure 24:
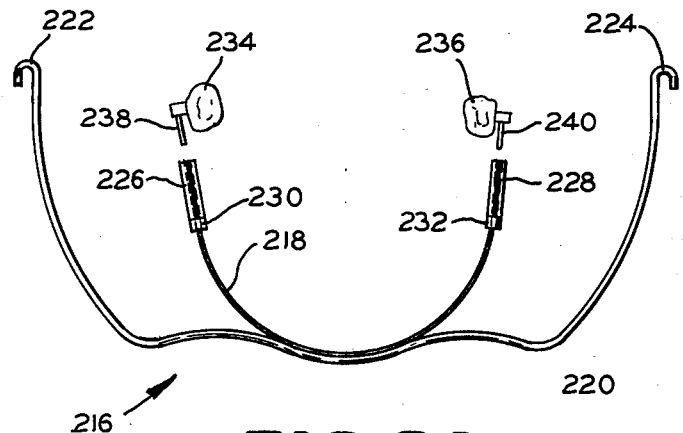
FIG. 24 is a plan view of face bow utilizing an alternate embodiment of the present invention.

Referring to FIG. 24, there is shown a face bow 216 having an inner arch 218 connected to an outer arch 220. The outer arch 220 has a pair of loops 222 and 224 formed at the ends thereof by which the face bow is attached to a head gear (not shown) which applies a pulling force to the outer arch 220 and the inner arch 218. In a conventional orthodontic system the end portions of the inner arch 218 would be inserted into a pair of upper buccal tubes similar to the upper buccal tube 182 of FIG. 20 and secured in place by a fixed stop member. In the present invention, the ends of the inner arch are inserted into a pair of tubular elastomeric coils 226 and 228 against a pair of stop members 230 and 232 which are attached to the inner arch 218. Each of a pair of teeth 234 and 236 has a rod member with an expanded base portion, 238 and 240 respectively, affixed thereto which replace the conventional buccal tubes. The elastomeric coils 226 and 228 can be slipped over the ends of the rod members 238 and 240 when the inner arch 218 is inserted into the patient's mouth. If the spacing between each of the stop members and the expanded base portion of the associated rod member is less than the length of the elastomeric coils, the elastomeric coils will be compressed and will apply a gently continuous force to the teeth as well as act as shock absorbers. If there is no need to replce the elastomeric coils 226 and 228, they may be molded onto the end portions of the inner arch 218 and the stop members 230 and 232 could be eliminated.

While mention has been made in the foregoing description that the material for forming the invention is a vinyl polymer, it will be understood that other materials having elastomeric porperties can be utilized to achieve the objectives of the invention. Other materials which could be utilized include urethane polymers having the desired physical characteristics.

In accordance with the provisions of the patent statues, I have explained the principles and mode of operation of my invention and have illustrated and described what I now consider to represent its best embodiment. However, I desire to have it understood that the invention may be practiced otherwise than as specifically illuatrated and described without departing from its spirit or scope.

What I claim is:

1. An orthodontic apparatus for use with an arch wire in straightening teeth comprising:

a band for attaching the orthodontic apparatus to a tooth;

a bracket formed of an elastomeric material and attached to said band, said bracket including a base portion and at least one arch wire receiving means integral with said base portion, said arch wire receiving means having a horizontal slot defined in the buccal surface thereof; and a liner retained in the horizontal slot of said arch wire receiving means and formed of a material substantially more rigid than said elastomeric material, said liner defining an opening at the buccal surface thereof and having a plurality of retaining tips formed on the upper and lower walls of the opening at a distance which is slightly less than the diameter of the arch wire whereby said liner is resiliently yieldable for snap engagement of the arch wire and said elastomeric arch wire receiving means is deflected during said snap engagement.

2. An orthodontic apparatus as defined in claim 1 wherein said elastomeric material is a vinyl polymer.

3. An orthodontic apparatus as defined in claim 1 wherein said elastomeric material is tooth colored.

4. An orthodontic apparatus as defined in claim 1 wherein said elastomeric material is transparent.

5. An orthodontic apparatus as defined in claim 1 wherein said band is formed of an elastomeric material.

6. An orthodontic apparatus for use with a ligature wire in straightening teeth comprising:

a band for attaching the orthodontic apparatus to a tooth; and a bracket formed of an elastomeric material and attached to said band, said bracket including:

a base portion;

at least one arch wire receiving means attached to said base portion; and an upstanding wing formed on said arch wire receiving means, said wing having a generally triangularly shaped tying wing tip with a substantially horizontal aperture formed therein for receiving one end of the ligature wire whereby, when the other end of the ligature wire is fixed with respect to said tooth, said wing tip may be deflected to exert a continuous gentle pressure on said tooth.

7. An orthodontic apparatus as defined in claim 6 wherein said arch wire receiving means has a substantially vertical aperture formed therein, said vertical aperture defining at least one pin retaining cavity of a larger diameter than the diameter of said vertical aperture for receiving an enlarged portion of an attachment pin.

8. An orthodontic apparatus as defined in claim 7 including an attachment pin having an enlarged shank portion receivable in said pin retaining cavity.

* * * * *